(12) United States Patent
Spycher et al.

(10) Patent No.: US 9,433,424 B2
(45) Date of Patent: Sep. 6, 2016

(54) MEMBRANE SWITCH ASSEMBLY FOR A HANDPIECE FOR CARRYING OUT MEDICAL INTERVENTIONS

(71) Applicant: Karl Storz GmbH & Co. KG, Tuttlingen (DE)

(72) Inventors: Raphael Spycher, Eschenz (CH); Markus Simmen, Schwerzenbach (CH)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/553,467

(22) Filed: Nov. 25, 2014

(65) Prior Publication Data
US 2015/0150566 A1 Jun. 4, 2015

(30) Foreign Application Priority Data

Nov. 27, 2013 (DE) .................. 10 2013 224 213

(51) Int. Cl.
*A61B 17/16* (2006.01)
*H01H 13/06* (2006.01)
(Continued)

(52) U.S. Cl.
CPC ..... *A61B 17/1622* (2013.01); *A61B 17/32002* (2013.01); *G05G 25/04* (2013.01); *H01H 13/06* (2013.01); *H01H 13/704* (2013.01); *H01H 13/7065* (2013.01); *H01H 13/86* (2013.01); *A61B 17/1617* (2013.01); *A61B 2017/0046* (2013.01); *A61B 2017/00367* (2013.01); *A61B 2017/00473* (2013.01); *A61B 2017/1602* (2013.01); *H01H 9/04* (2013.01); *H01H 2009/066* (2013.01); *H01H 2215/034* (2013.01); *H01H 2221/002* (2013.01); *H01H 2223/002* (2013.01); *H01H 2227/026* (2013.01); *H01H 2300/014* (2013.01)

(58) Field of Classification Search
CPC ................. H01H 2009/066; H01H 2227/026; H01H 2300/014; H01H 9/04; H01H 13/06; H01H 2221/002; H01H 13/86; H01H 13/7065; H01H 13/704; H01H 2223/002; H01H 2215/034
USPC ........... 200/5 A, 302.1–302.3, 293–296, 341
See application file for complete search history.

(56) References Cited

U.S. PATENT DOCUMENTS 5,430,266 A * 7/1995 Austin, Jr. ........... H01H 13/702
174/521
6,500,169 B1 12/2002 Deng
(Continued)

FOREIGN PATENT DOCUMENTS

CN 203026410 U 6/2013
DE 202008007136 U1 10/2009
(Continued)

OTHER PUBLICATIONS

European Office Action Application No. 14193127.9 Issued: Apr. 8, 2016 6 pages.

*Primary Examiner* — Edwin A. Leon
(74) *Attorney, Agent, or Firm* — Whitmyer IP Group LLC (57) ABSTRACT

A membrane switch assembly for a handpiece for carrying out medical interventions includes a ring-like support surrounding a support interior, and a keypad element arranged on the support and intended to be actuated in order to carry out switching procedures. The keypad element is secured on the support so as to close the support interior in a fluid-tight manner. On an outer circumferential side of the ring-like support, a sealing arrangement surrounds the ring-like support.

17 Claims, 7 Drawing Sheets

(51) Int. Cl.
*G05G 25/04* (2006.01)
*H01H 13/704* (2006.01)
*H01H 13/7065* (2006.01)
*H01H 13/86* (2006.01)
*A61B 17/32* (2006.01)
*H01H 9/04* (2006.01)
*H01H 9/06* (2006.01)
*A61B 17/00* (2006.01)

(56) References Cited

U.S. PATENT DOCUMENTS

| | | |
|---|---|---|
| 8,115,126 B2 | 2/2012 | Deng et al. |
| 8,594,597 B2 | 11/2013 | Saito et al. |
| 2001/0017255 A1 | 8/2001 | Katsumi |
| 2003/0160669 A1* | 8/2003 | Trandafir ............ H01H 13/702 335/78 |
| 2004/0099430 A1 | 5/2004 | Scudder |
| 2004/0201512 A1 | 10/2004 | Sugimoto et al. |
| 2013/0292235 A1 | 11/2013 | Baum et al. |

FOREIGN PATENT DOCUMENTS

| | | |
|---|---|---|
| EP | 2319419 A1 | 5/2011 |
| FR | 2931996 A1 | 12/2009 |
| JP | 2002075110 A | 3/2002 |

* cited by examiner

MEMBRANE SWITCH ASSEMBLY FOR A HANDPIECE FOR CARRYING OUT MEDICAL INTERVENTIONS

FIELD OF THE INVENTION

The present invention relates to a membrane switch assembly for a handpiece that can be used for carrying out medical interventions, in particular surgical interventions.

BACKGROUND OF THE INVENTION

U.S. Pat. No. 6,500,169 B1 discloses a handpiece for carrying out medical interventions. This handpiece contains a drive for a surgical tool that is to be fitted on the handpiece. An example of a surgical tool of this kind is an orthopedic shaver, with which material, for example tissue or bone material, can be removed inside a body during drilling or milling procedures. A membrane switch assembly is arranged on this known handpiece, with three actuation regions which are arranged in a row and are to be acted on manually and, upon manual actuation, act on switch elements and thus permit activation or control of the drive provided in the handpiece. The three actuation regions arranged in a row are formed on a plate-like, flexible keypad element. The keypad element is arranged covering a recess on the handpiece. A plate-like cover element positioned to engage over the keypad element is secured on the handpiece by a plurality of fastening screws and presses an outer edge area of the keypad element against an abutment surface of the handpiece in order to produce a fluid-tight seal.

SUMMARY OF THE INVENTION

It is an object of the present invention to make available a membrane switch assembly for a handpiece for carrying out medical interventions, which with a simple and reliable structure allows a fluid-tight seal to be produced with respect to a handpiece receiving the membrane switch assembly.

According to the invention, this object is achieved by a membrane switch assembly for a handpiece for carrying out medical interventions, comprising:
  a ring-like support surrounding a support interior,
  a keypad element arranged on the support and intended to be actuated in order to carry out switching procedures, wherein the keypad element is secured on the support so as to close the support interior in a fluid-tight manner, and,
  on an outer circumferential side of the ring-like support, a sealing arrangement surrounding the ring-like support.

In the structure according to the invention, the ring-like support and the keypad element secured thereon form a unit, which in itself already ensures that, in the area where the keypad element adjoins the ring-like support, the fluid-tight closure that is produced there prevents entry of fluid. The fluid-tight connection of the support itself to a handpiece receiving it is effected by the sealing arrangement provided on the outer circumferential side of the support. Thus, the membrane switch assembly has a structure that is easy to produce, where in particular the fluid-tight connection to a handpiece receiving it is not produced by a planar sealing element pressed by an additional component, but instead is produced by a sealing arrangement arranged on the outer circumferential side of the ring-like support and thus acting substantially radially. The provision of a fluid-tight closure of this kind, while avoiding the formation of small structures as may occur especially in the area of fastening screws, is of great importance especially when performing cleaning procedures, particularly of appliances of this kind that are to be used in the area of surgical interventions.

In order to be able to obtain the fluid-tight connection of the keypad element to the ring-like support in a particularly simple and reliable way, it is proposed that the keypad element has a substantially plate-like shape and, to permit the fluid-tight securing on the support, has a securing flange engaging at least partially over a front face of the support and/or has a securing wall engaging in the support interior and bearing on an inner circumferential side of the support.

The keypad element is secured on the support advantageously by material bonding, preferably vulcanization. Vulcanization ensures, on the one hand, that a fluid-tight bond is obtained and, on the other hand, that such a bond can be subjected to considerable mechanical loading.

A particularly simple structure, which nonetheless provides optimal sealing of the membrane switch assembly with respect to a handpiece receiving it, can be obtained if the sealing arrangement on the outer circumferential side of the support comprises, in at least one sealing element receiving groove, at least one sealing element like an O-ring.

The sealing action of the sealing arrangement can be obtained particularly effectively and in a structurally simple way if the support has a substantially round, preferably circular, outer circumferential contour. The substantially round configuration avoids the formation of corner areas or edge areas where the sealing action could be weakened. It should be noted that a circular configuration is particularly advantageous since, with a predefined cross-sectional surface area, the circumference to be sealed is minimized. However, an elliptic, oval or similarly shaped outer circumferential contour could in principle also be provided.

To allow an electrically excitable appliance, for example an electric drive motor, to be controlled and activated or deactivated by the membrane switch assembly, it is proposed that a switch arrangement, with at least one switch element that can be acted on by the keypad element, is provided. The switch arrangement can comprise a switch plate, for example a printed circuit board, arranged substantially in the support interior and carrying at least one switch element.

To ensure a defined interaction between the keypad element and the at least one switch element provided on the switch plate, it is proposed that a positioning formation is provided on the keypad element and/or on the support, and that, on the switch plate, a counter-positioning formation is provided that interacts with the positioning formation to predefine a predetermined positioning for the switch plate in the support interior.

This positioning interaction can be easily achieved if one formation of positioning formation and counter-positioning formation, preferably the positioning formation, comprises at least one positioning projection, and the other formation of positioning formation and counter-positioning formation, preferably the counter-positioning formation, comprises at least one positioning recess receiving at least one positioning projection.

When carrying out switching procedures, the generally flexible keypad element is actuated, for example manually, and thus deformed. To ensure a defined interaction here between the keypad element and the switch arrangement, it is further proposed that the keypad element has an actuation region assigned to at least one switch element, preferably assigned to each switch element.

In an embodiment which, on the one hand, helps avoid actuating errors and, on the other hand, ensures a defined action on a predetermined switch element, provision can be made that at least one actuation region comprises a first actuation formation, preferably a first actuation projection, provided on an outer face of the keypad element oriented away from the support interior, and/or a second actuation formation, preferably a second actuation projection, provided on an inner face of the keypad element oriented toward the support interior.

In manual actuation of the membrane switch assembly, it is of particular importance that an operator, for example a physician, is able to tell, during a surgical intervention, that a switching procedure actually also takes place when the keypad element is acted on. For this purpose, a preferably monostable actuation resistance element counteracting the actuation of the keypad element can be provided and assigned to at least one switch element, preferably assigned to each switch element. When the keypad element is loaded, the actuation resistance element generates a resistance which indicates to the operator that the keypad element has been actuated to a sufficient extent.

To ensure that an actuation resistance element of this kind is assigned in a defined manner to a switch element of the switch arrangement, it is proposed that at least one actuation resistance element is fixed in relation to the switch arrangement by a fixing layer, preferably adhesive film.

The invention further relates to a handpiece for carrying out medical interventions, in particular surgical interventions, comprising at least one membrane switch assembly constructed according to the invention, wherein a membrane switch seat provided in the handpiece is assigned to and receives the at least one membrane switch assembly.

The fluid-tight connection of the membrane switch assembly to the handpiece can advantageously be achieved if the sealing arrangement bears in a fluid-tight manner on an inner circumferential surface surrounding the membrane switch seat. This fluid-tight and generally prestressed contact can at the same time also serve to hold the entire membrane switch assembly in a fixed position on the handpiece. Provision can furthermore be made that at least one retaining step is provided on the membrane switch seat. This retaining step can on the one hand serve to form an insertion abutment for the membrane switch assembly, when the latter is inserted into the membrane switch seat, and thereby provide a defined positioning of the membrane switch assembly in the membrane switch seat. Moreover, this at least one retaining step can serve to ensure that the switch arrangement positioned in the support interior does not fall out of the support interior. No further structural measures are then needed to ensure that the switch arrangement is substantially secure on the support.

BRIEF DESCRIPTION OF THE DRAWINGS

The present invention is described in detail below with reference to the attached figures, in which.

DETAILED DESCRIPTION OF THE INVENTION

Figure 1:
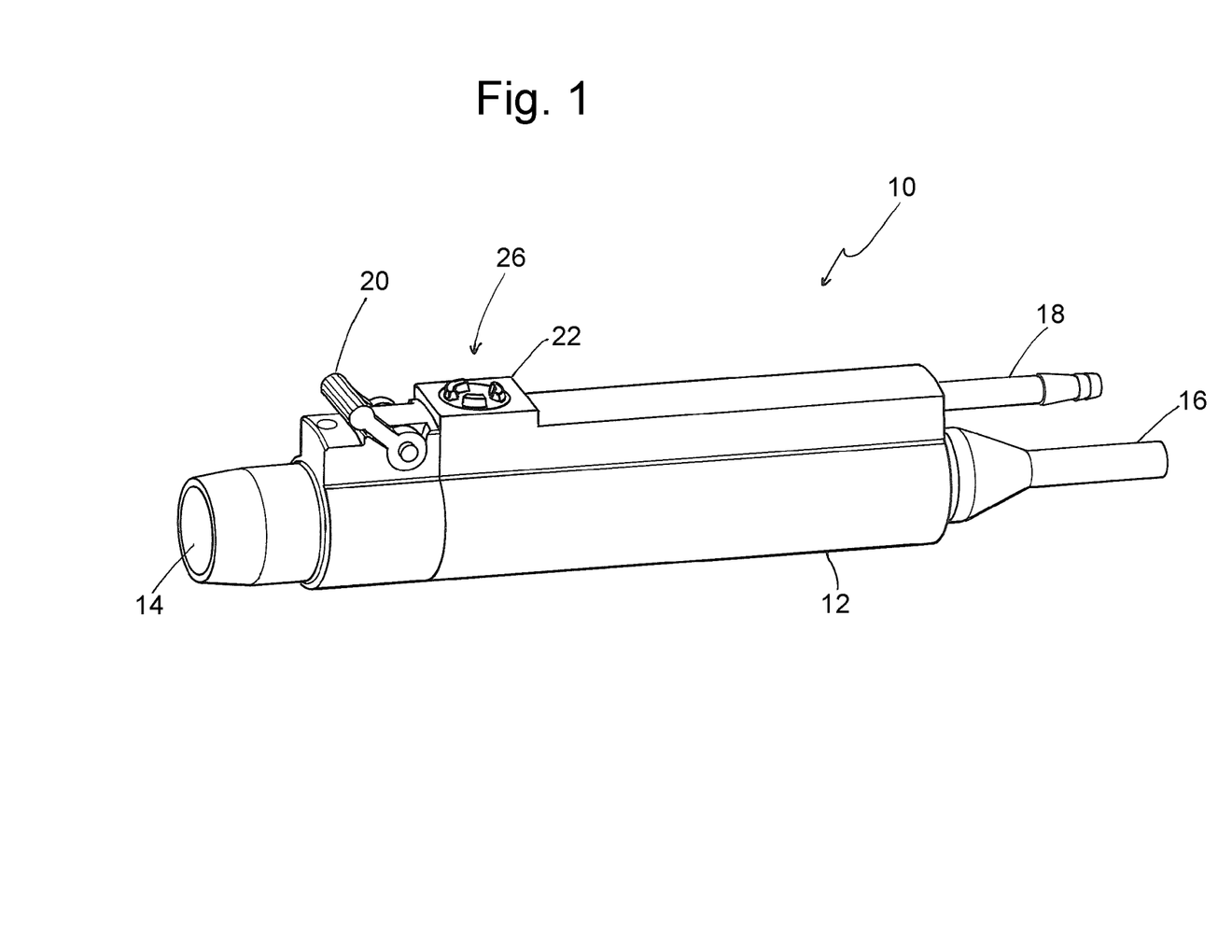
FIG. 1 shows a perspective view of a handpiece for carrying out medical interventions.

In FIG. 1, a handpiece that can be used for carrying out medical interventions is designated generally by 10. In a handpiece housing 12, the handpiece 10 contains a drive, for example an electromotive drive, for a surgical tool (not shown in FIG. 1) to be secured on the handpiece 10. This surgical tool can be inserted in an end region shown on the left in FIG. 1, particularly in an opening 14 provided there, and can be coupled to the drive accommodated in the handpiece housing 12, such that this surgical tool can be driven, for example, for rotation about its longitudinal axis. For example, this surgical tool can be designed as an orthopedic shaver, with which tissue or bone material can be removed in a body, for example a human body. To supply it with electrical power, a connection cable 16 is provided on the handpiece 10. A connection stub 18 is also provided on the handpiece 10. A suction line can be attached to this connection stub 18, such that material removed by the surgical tool during an operation can be conveyed, through a hollow cavity formed in the interior of this tool, into the handpiece 10 and out through the connection stub 18. Irrigation liquid introduced into the area where such an operation is performed can also be aspirated through the handpiece 10 in this way. To trigger this suction function, an actuating lever 20 is provided on the handpiece 10, which actuating lever 20 can be actuated manually and thus pivoted, in order to actuate a valve provided in the handpiece 10 for preferably stepless release of a flow path through the handpiece 10.

Figure 2:
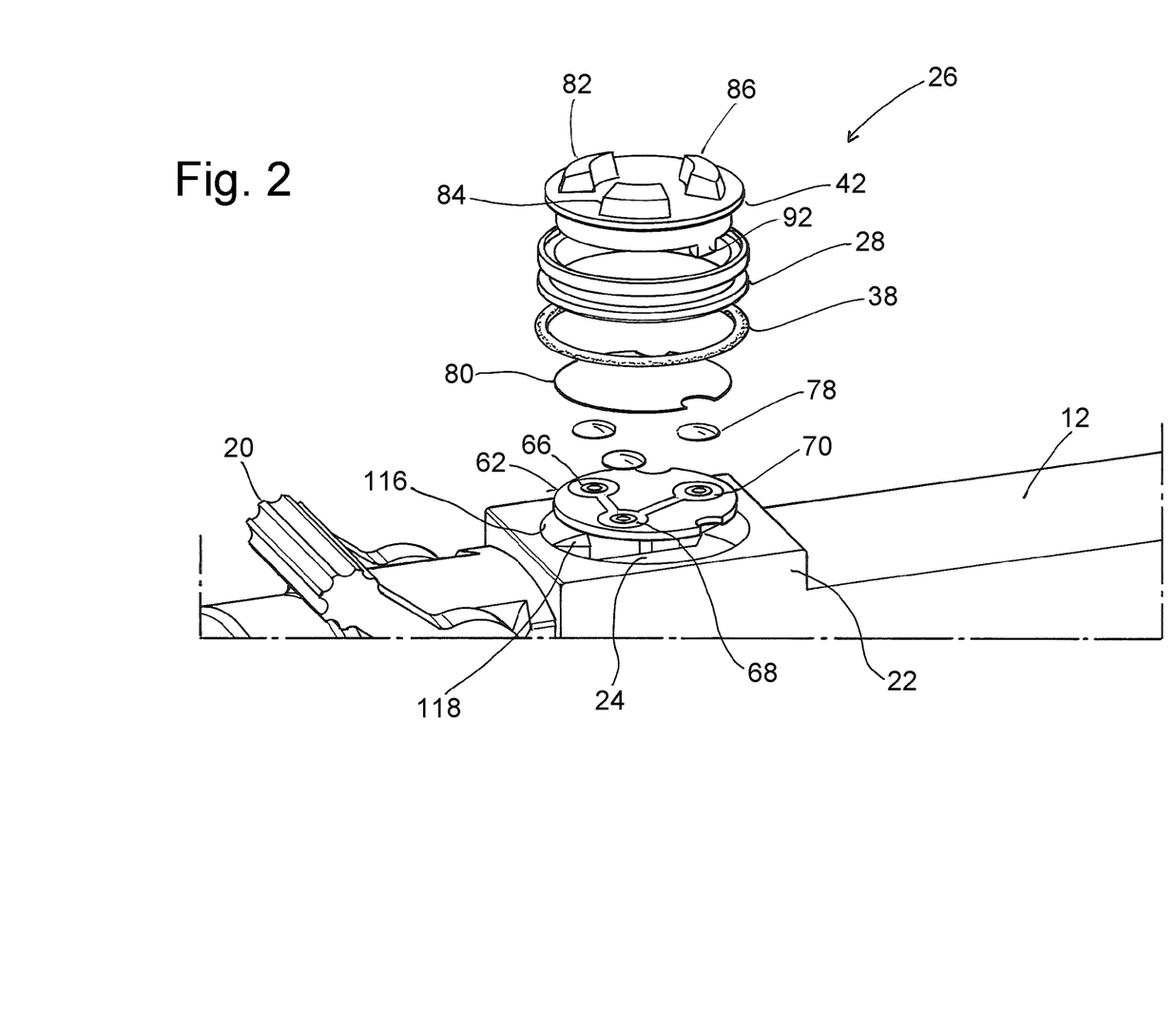
FIG. 2 shows an enlarged detail view of the handpiece from FIG. 1, with a membrane switch assembly shown in an exploded view over a membrane switch seat.

As can also be seen from FIG. 2, a membrane switch seat 24 is formed in what is for example a raised area 22 of the handpiece housing 12. A membrane switch assembly 26 described in detail below is inserted into this membrane switch seat 24 in such a way that, by manual actuation, the drive provided in the handpiece 10, for example an electrically excitable drive motor, can be controlled and activated or deactivated.

Figure 3:
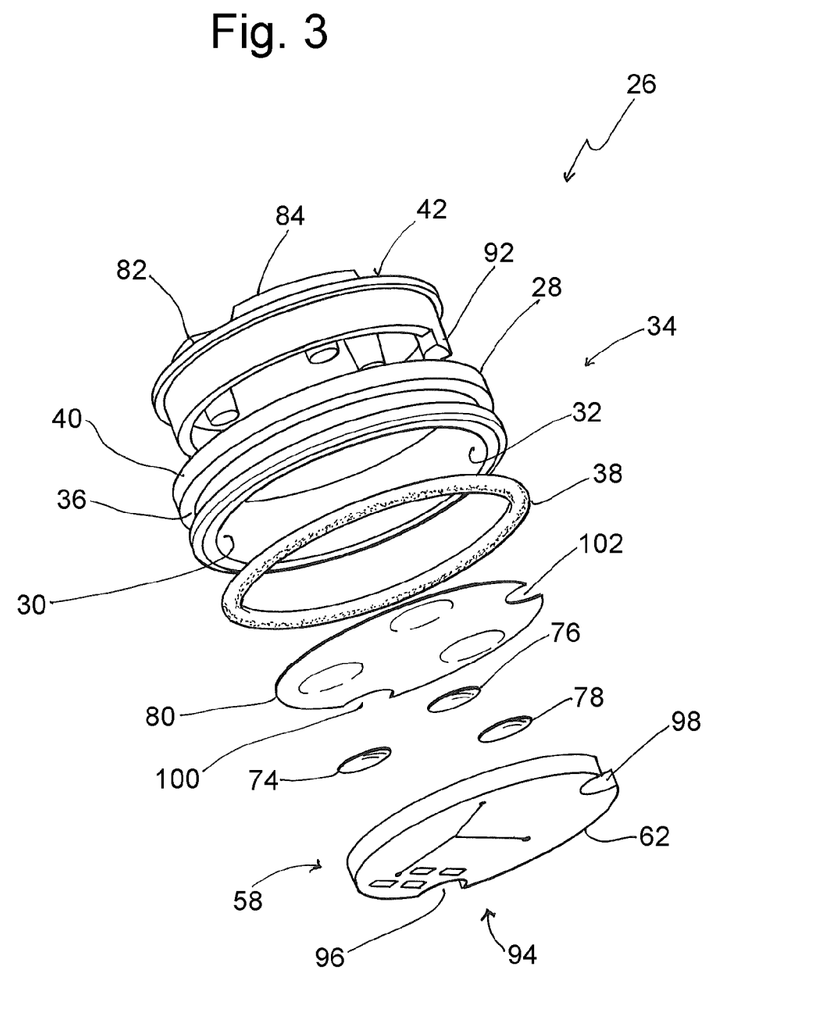
FIG. 3 shows the membrane switch assembly in an enlarged exploded view.
Figure 4:
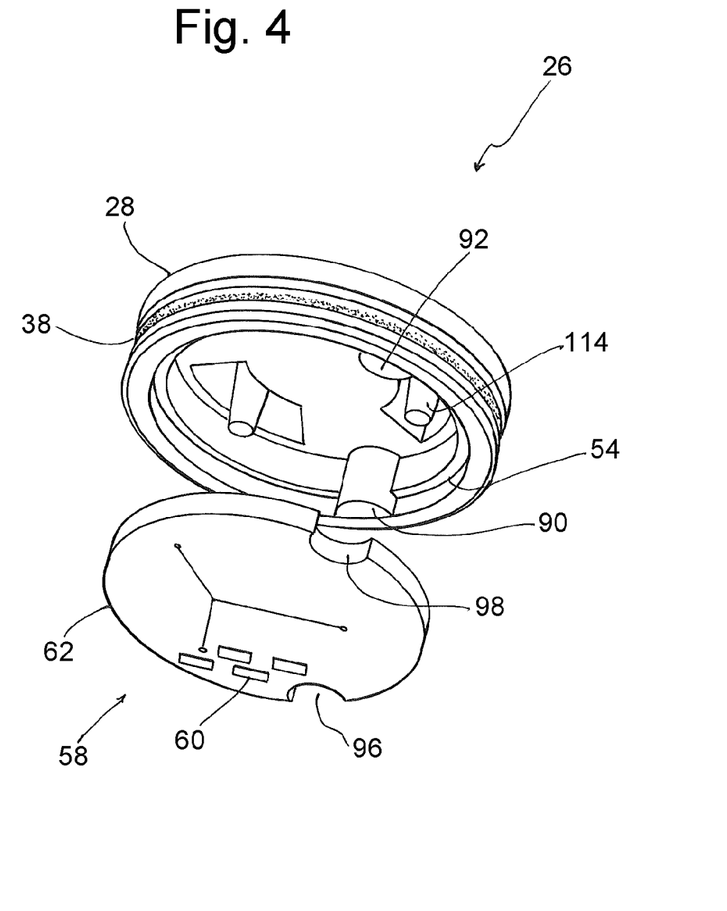
FIG. 4 shows an exploded perspective view of a ring-like support provided with a sealing arrangement and with a keypad element, and a switch arrangement of the membrane switch assembly to be positioned in a support interior.

The membrane switch assembly 26, also shown in FIG. 3 in an exploded view, has, as its central component, a ring-like support 28 advantageously made of metal, for example stainless steel. On its inner circumferential side 30, the ring-like support 28 is formed, for example, with a substantially plane, i.e. cylindrical, inner circumferential surface 32. On its outer circumferential side 34, the ring-like support 28 has a groove 36 which extends over the entire circumference, preferably with substantially constant width and/or depth, and opens radially outward with respect to a longitudinal center axis of the ring-like support 28. When the membrane switch assembly 26 is assembled, a sealing element 38 like an O-ring is arranged in this groove 36, specifically in such a way that it protrudes beyond an outer circumferential surface 40 of the ring-like support 28 in the unloaded state.

For manual actuation, for example by a physician performing a surgical intervention, the membrane switch assembly 26 has a keypad element 42 which has, for example, a substantially plate-like shape and is made from an elastomer material, i.e. is flexible. In the cross-sectional view in FIG. 5, it will be seen that the keypad element 42 has a plate-like body 44 which, in its radially outer area, radially with respect to a longitudinal center axis L of the ring-like support 28, provides a securing flange 50, which is received in a corresponding indentation in a front face 48 of the ring-like support 28. Thus, the body 44 of the keypad element 42 lies substantially flush with a front surface 52 of the support 28 in this area.

Figure 5:
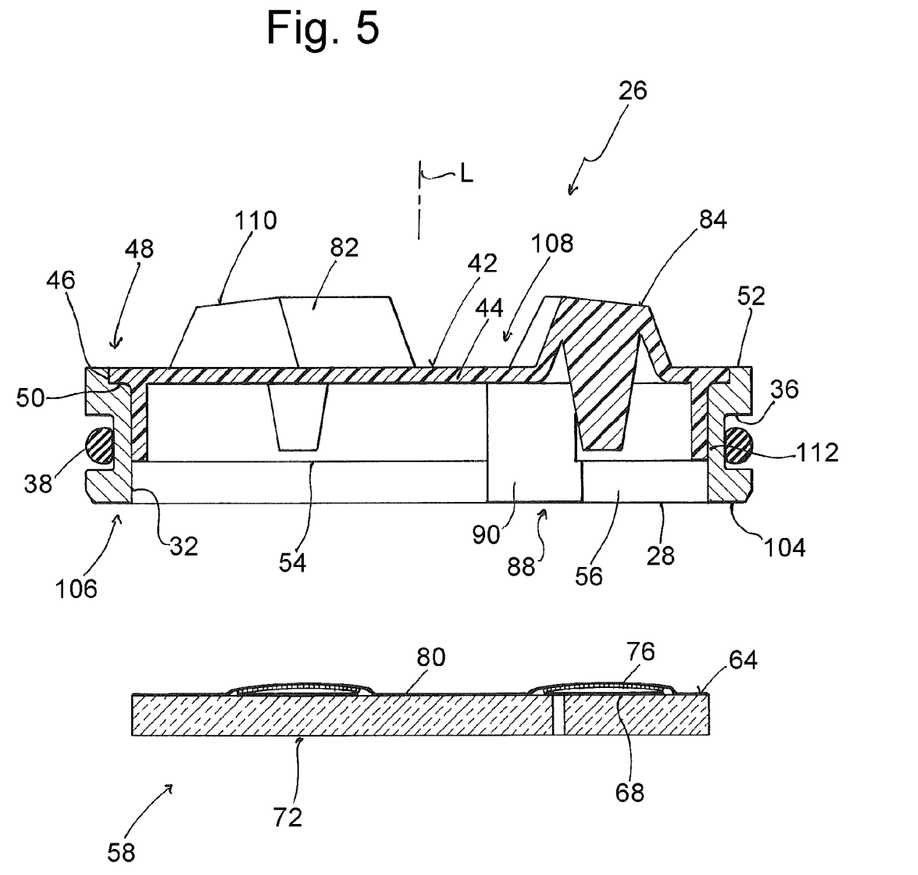
FIG. 5 shows an exploded view, corresponding to FIG. 4, in cross section.
Figure 6:
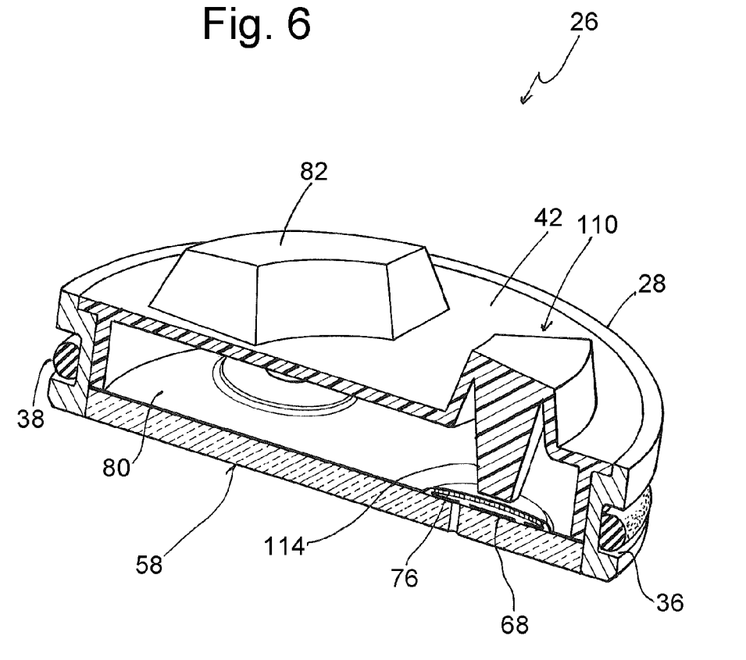
FIG. 6 shows a perspective cross-sectional view of the membrane switch assembly in the assembled state.
Figure 7:
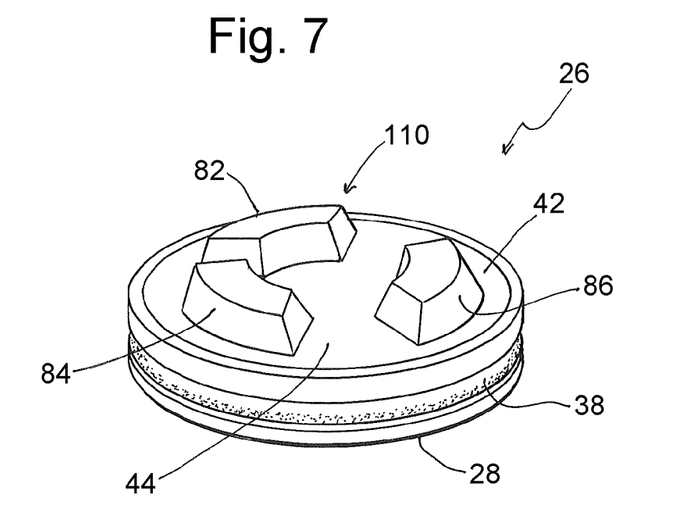
FIG. 7 shows a perspective view of the membrane switch assembly from above.
Figure 8:
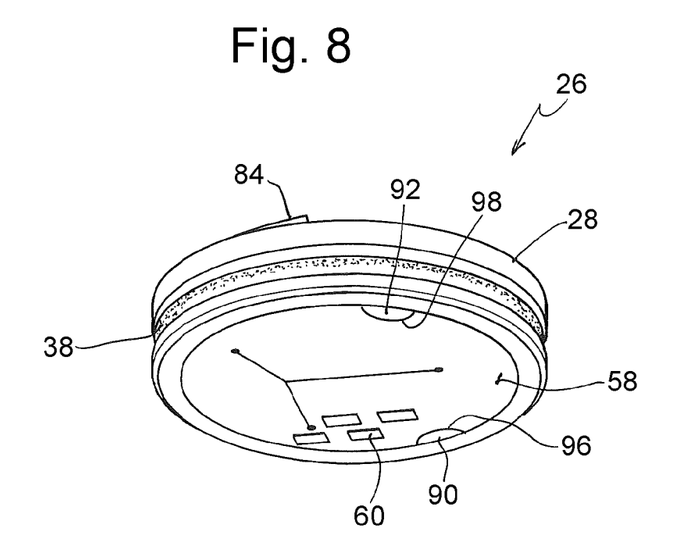
FIG. 8 shows a perspective view of the membrane switch assembly from below.

A securing wall 54, preferably of substantially cylindrical configuration, extends from the plate-like body 44 in such a way that it bears on the inner circumferential surface 32 of the support 28 when the securing flange 50 is received in the indentation 46. In the area where the securing flange 50 and/or the securing wall 54 of the keypad element 42 bears on the ring-like support 28, these two structural parts are preferably rigidly connected to each other by a material bond and therefore also in a fluid-tight manner. This material bond can be obtained particularly advantageously by vulcanization of the keypad element 42 made, for example, from elastomer material. The use of adhesive or the like is also possible in principle. The ring-like support 28 and the keypad element 42 thus form a rigidly interconnected structural unit which, in the direction of the front face 48 of the ring-like support, closes a support interior 56 of the latter in a fluid-tight manner.

The membrane switch assembly 26 further comprises a switch arrangement designated generally by 58. This switch arrangement 58 has a switch plate 62 constructed, for example, in the manner of a printed circuit board, e.g. substantially cylindrical and carrying a plurality of conductor tracks and also contacts 60. On an inner face 64 of the switch arrangement 58 to be positioned facing toward the support interior 56, the switch plate 62, in the example shown, carries three switch elements 66, 68, 70. Each of these switch elements 66, 68, 70, which can be positioned in a triangular or annular configuration on the switch plate 62 as shown in FIG. 2, can serve to close an electrical contact, for example, in order to control an electrically excitable drive motor in a defined manner. The electrical connection between the switch arrangement 58 and further conductor elements provided in the handpiece 10 can take place via the contacts 60, e.g. solder contacts, on an outer face 72 of the switch arrangement 58 to be positioned facing away from the support interior 56.

Assigned to each of the three switch elements 66, 68, 70, an actuation resistance element 74, 76, 78 can be provided. These actuation resistance elements, which are curved and wafer-like for example and advantageously monostable, are positioned over the switch elements 66, 68, 70 and are held on the switch plate 62 by an adhesive film 80, e.g. polyimide film. An outer circumferential contour of the adhesive film 80 can correspond substantially to the outer circumferential contour of the switch plate 62.

Assigned to each of the three switch elements 66, 68, 70, an actuation region 82, 84, 86 is provided on the keypad element 42. The actuation regions 82, 84, 86 are substantially identical to one another in design and are positioned on the keypad element 42 such that they lie over the respectively associated switch elements 66, 68, 70 and the actuation resistance elements 74, 76, 78. To ensure this defined relative positioning, a positioning formation 88 is provided on the keypad element 42. This positioning formation 88 comprises, on two circumferential areas, positioning projections 90, 92 which, in the area of the securing wall 54, protrude axially beyond the latter and, for example, also extend radially inward. The switch arrangement 58, or switch plate 62 thereof, and also the adhesive film 80 are provided with positioning recesses 96, 98 and 100, 102, respectively, in order to make available a counter-positioning formation 94. In the assembled state, the positioning projections 90, 92 engage in the positioning recesses 96, 98 of the switch plate 62 and ensure that, when the switch arrangement 58 is positioned in the support interior 56, said switch arrangement 58 has a defined position relative to the keypad element 42 and cannot turn. In order also to ensure a defined axial positioning relative to the longitudinal center axis L of the ring-like support 28, the securing wall 54 of the keypad element 42 can, for example, extend so far into the support interior 56 that an insertion abutment for the switch arrangement 58 is thereby formed, with the result that, in the assembled state, the rear face 72 of the switch arrangement 58 can lie substantially flush with a front surface 104 on a front end 106 of the ring-like support 28.

The already discussed actuation regions 82, 84, 86 of the switch element 42 have dome-like first actuation projections 110, which extend from the plate-like body 44 of the keypad element 42, on an outer face 108 thereof, in the direction away from the support interior 56. For a physician using the handpiece 10, these actuation projections 110 can be operated by the finger used for the actuation, for example by the thumb, such that, depending on which of the switch elements 66, 68, 70 is to be acted on, the actuation projection 110 of the associated actuation region 82, 84, 86 is actuated, i.e. subjected to pressure.

Furthermore, in the area of a respective first actuation projection 110, each actuation region 82, 84, 86 has a second actuation projection 114 arranged on an inner face 112 of the plate-like body 44 of the keypad element 42 and extending in the direction into the support interior 56. Each of these second actuation projections 114 is dimensioned such that, in the unloaded state, it lies, for example, a short distance above a respectively associated switch element 66, 68, 70 and actuation resistance element 74, 76, 78. When the first actuation projection 110 of an actuation region 82, 84, 86 is pressed, and thus moved in the direction of the support interior 56, the associated second actuation projection 114 also moves accordingly in the direction of the associated switch element 66, 68 or 70. In the course of this movement, this second actuation projection 114 comes into contact with the adhesive film 80 and thus stresses the actuation resistance element 74, 76 or 78 lying under the latter. This monostable component first of all generates a clearly palpable resistance but then yields even under minimal stress, such that, during the continued movement of the second actuation projection 114, the latter also loads the switch element 66, 68 or 70 and, for example, closes an electrical contact of this switch element. Thus, the transition of a respective actuation resistance element 74, 76, 78 to its non-stable state shows an operator that the respective actuation region 82, 84 or 86 has been loaded to such an extent that the associated switch element 66, 68, 70 has also been activated.

If the actuation effect is decreased or cancelled, the keypad element 42 returns to its original shape by virtue of its elasticity. The previously active second actuation projection 114 then frees the switch element 66, 68 or 70 interacting with it, such that, for example, the previously established electrical contact is interrupted again and the associated actuation resistance element also returns to its stable state.

It will be noted here that, in the illustrative embodiment shown in the figures, the number and also the positioning of the switch elements 66, 68, 78, and also of the components and portions thereof interacting therewith, are chosen only by way of example. A greater or lesser number of switch elements could of course also be provided. The choice of the number of switch elements can be made depending on which and how many functions are to be implemented by a membrane switch assembly 26 of this kind. These functions can comprise, for example, the switching on and off of an electric motor for a surgical tool, the predefining of the direction of rotation, the predefining of the speed and the operating mode, i.e. drilling or milling for example. The membrane switch assembly can also be used, by interaction of the keypad element 42 with the switch arrangement 58, to realize a dimmer functionality in which, controlled for example by the duration of the actuation of the keypad element 42, it is possible to achieve a stepless variation in the speed of an electric motor.

After it has been assembled, the membrane switch assembly 26 with the above-described structure is inserted into the membrane switch seat 24 provided in the handpiece housing 12. The geometry or contour of an inner circumferential surface 116 of the membrane switch seat 24 advantageously corresponds to the outer circumferential contour of the support 28. A circular contour is advantageously chosen here in each case. With a minimal circumference of the membrane switch assembly, this avoids the formation of corner-like or edge-like areas, which can be sealed off only with difficulty against the entry of fluid.

Assigned to the membrane switch seat 24 is at least one retaining step 118, preferably a plurality of retaining steps 118, which protrude inward beyond the inner circumferential surface 116. These retaining steps 118, or one retaining step extending circumferentially like a ring for example can on the one hand form an insertion abutment for the entire membrane switch assembly 26, in order thereby to provide a defined installation position when the membrane switch assembly is inserted into the handpiece housing 12. On the other hand, with retaining steps 118 of this kind, the switch arrangement 58 can be held in a defined position relative to the ring-like support 28. This means that no additional fixing measures have to be provided for the switch arrangement 58 in order to hold the latter in the support interior 56. Similarly, in a pre-assembly state, the switch arrangement 58 could be prevented from falling out of the ring-like support by means of an interference fit that is generated when the switch arrangement 58 is inserted into the support interior 56, for example an interference fit of the positioning projections 90, 92 in the positioning recesses 96, 98.

The membrane switch assembly 26 is fixed in the membrane switch seat 24 by the sealing element 38 on the handpiece housing 12 pressing radially outward against the inner circumferential surface 116. The sealing element 38 is supported radially inward on the base of the groove 38 of the support 28 and radially outward on the inner circumferential surface 116 lying opposite and at a slight distance from the outer circumferential surface 40. Thus, the sealing element 38 not only has the function of sealing the membrane switch assembly 26 with respect to the handpiece housing 12, but also performs the function of fixing the membrane switch assembly 26 on the handpiece housing 12. This avoids the need to use additional fixing members, e.g. screws or the like, which entail the danger of forming undercut areas or internal spaces that can be accessed only with difficulty for cleaning procedures.

With the design of a membrane switch assembly according to the invention for a handpiece for carrying out medical interventions or of a handpiece designed with such a membrane switch assembly, a fluid-tight connection of the membrane switch assembly to a handpiece housing is ensured with a simple structure and without additional securing members being required for this purpose. Of importance here is the use of a radially active sealing arrangement which ensures not only the fluid-tight connection but also the fixing of the membrane switch assembly on the handpiece housing. It goes without saying that several such membrane switch assemblies can be provided on a handpiece, if appropriate also with a different number of switching functions.

The invention claimed is:

1. A membrane switch assembly for a handpiece for carrying out medical interventions, comprising:
    a ring-like support surrounding a support interior,
    a keypad element arranged on the support and intended to be actuated in order to carry out switching procedures, wherein the keypad element is secured on the support so as to close the support interior in a fluid-tight manner, and,
    on an outer circumferential side of the ring-like support, a sealing arrangement surrounding the ring-like support.

2. The membrane switch assembly as claimed in claim 1, wherein the keypad element has a substantially plate-like shape and, to permit the fluid-tight securing on the support, has a securing flange engaging at least partially over a front face of the support and/or has a securing wall engaging in the support interior and bearing on an inner circumferential side of the support.

3. The membrane switch assembly as claimed in claim 1, wherein the keypad element is secured on the support by material bonding.

4. The membrane switch assembly as claimed in claim 1, wherein the sealing arrangement on the outer circumferential side of the support comprises, in at least one sealing element receiving groove, at least one O-ring sealing element.

5. The membrane switch assembly as claimed in claim 1, wherein the support has a substantially round outer circumferential contour.

6. The membrane switch assembly as claimed in claim 1, wherein a switch arrangement, with at least one switch element that can be acted on by the keypad element, is provided.

7. The membrane switch assembly as claimed in claim 6, wherein the switch arrangement comprises a switch plate arranged substantially in the support interior and carrying at least one switch element.

8. The membrane switch assembly as claimed in claim 7, wherein a positioning formation is provided on the keypad element and/or on the support, and, on the switch plate, a counter-positioning formation is provided that interacts with the positioning formation to predefine a predetermined positioning for the switch plate in the support interior.

9. The membrane switch assembly as claimed in claim 8, wherein one formation of positioning formation and counter-positioning formation comprises at least one positioning projection, and the other formation of positioning formation and counter-positioning formation comprises at least one positioning recess receiving at least one positioning projection.

10. The membrane switch assembly as claimed in claim 6, wherein the keypad element has an actuation region assigned to at least one switch element.

11. The membrane switch assembly as claimed in claim 10, wherein at least one actuation region comprises a first actuation formation provided on an outer face of the keypad element oriented away from the support interior, and/or a second actuation formation provided on an inner face of the keypad element oriented toward the support interior.

12. The membrane switch assembly as claimed in claim 10,
wherein an actuation resistance element counteracting the actuation of the keypad element is provided and assigned to at least one switch element.

13. The membrane switch assembly as claimed in claim 12,
wherein at least one actuation resistance element is fixed in relation to the switch arrangement by a fixing layer.

14. A handpiece for carrying out medical interventions, comprising at least one membrane switch assembly as claimed in claim 1,
wherein a membrane switch seat provided in the handpiece is assigned to and receives the at least one membrane switch assembly.

15. The handpiece as claimed in claim 14,
wherein the sealing arrangement bears in a fluid-tight manner on an inner circumferential surface surrounding the membrane switch seat and/or at least one retaining step for the membrane switch assembly is provided on the membrane switch seat.

16. The membrane switch assembly as claimed in claim 1,
wherein the keypad element has a substantially plate-like shape and, to permit the fluid-tight securing on the support, has a securing flange engaging at least partially over a front face of the support and has a securing wall engaging in the support interior and bearing on an inner circumferential side of the support.

17. The membrane switch assembly as claimed in claim 1,
wherein the sealing arrangement is adapted to be secured to housing of the medical device in a fluid-tight manner when the assembly is inserted into the housing.

* * * * *